(12) United States Patent
Cecchi et al.

(10) Patent No.: US 7,015,031 B2
(45) Date of Patent: Mar. 21, 2006

(54) BIOLOGICAL SPECIMEN-CULTURING SYSTEM AND METHOD WITH ONBOARD SPECIMEN DEVELOPMENT SENSORS

(75) Inventors: Michael D. Cecchi, Madison, CT (US); Monica Mezezi, Guelph (CA)

(73) Assignee: Genx International, Inc., Guilford, CT (US)

( * ) Notice: Subject to any disclaimer, the term of this patent is extended or adjusted under 35 U.S.C. 154(b) by 169 days.

(21) Appl. No.: 10/053,944

(22) Filed: Jan. 24, 2002

(65) Prior Publication Data
US 2003/0138942 A1  Jul. 24, 2003

(51) Int. Cl.
*C12M 1/34* (2006.01)
(52) U.S. Cl. .............. 435/288.7; 435/303.1; 435/809
(58) Field of Classification Search ............ 435/303.1, 435/303.2, 809; 422/104; 219/218, 385, 219/428
See application file for complete search history.

(56) References Cited

U.S. PATENT DOCUMENTS

| | | | |
|---|---|---|---|
| 4,696,902 A | * | 9/1987 | Bisconte .................... 435/300 |
| 5,290,701 A | * | 3/1994 | Wilkins .................... 435/287.3 |
| 2002/0068358 A1 | * | 6/2002 | Campbell et al. ........ 435/289.1 |

* cited by examiner

Primary Examiner—David Redding
(74) Attorney, Agent, or Firm—William W. Jones

(57) ABSTRACT

A specimen culturing system and method is employed to culture biological specimens, preferably embryos. The embryos are cultured in an incubator in separate culturing sites, such as wells, which can each hold an embryo container, such as a Petrie dish, that contains one or more of the embryos. The culturing wells are disposed in one or more shelves in the incubator. The culturing containers are formed from a transparent material such as tempered glass. Each of the wells are provided with embryo development-monitoring adjuncts. The development-monitoring adjuncts are preferably embryo-imaging devices and sound-monitoring devices. The system includes image and sound recording components which can record periodic images of the embryos during the culturing cycle; and can record sounds emanating from the specimens. The embryo-imaging devices can include CCD imaging devices which are connected to image viewing and recording adjuncts by means of electrical connections. Each embryo development-monitoring site in the incubator can be provided with its own CCD embryo-imaging device which can be periodically activated by an incubator processor controller to produce and record images of the embryos at selected time intervals during the culturing cycle. The sound monitoring can be performed periodically or continuously during the culturing cycle. Both the imaging and sound monitoring can be recorded, and the resultant data can be chronologically stored so that a technician can monitor and review the embryo development without having to remove the embryos from the incubator. Images and audio signals can be digitized and transmitted from the incubator to remote worldwide sites for expert analysis and evaluation.

8 Claims, 4 Drawing Sheets

BIOLOGICAL SPECIMEN-CULTURING SYSTEM AND METHOD WITH ONBOARD SPECIMEN DEVELOPMENT SENSORS

TECHNICAL FIELD

This invention relates to a method and apparatus for culturing embryos, cells, tissues, or other biological specimens in a culturing environment which includes specimen development-monitoring sensors. One embodiment of this invention relates to an embryo culturing apparatus and method wherein individual embryos in the apparatus are monitored for growth development by integrated onboard sensors in the apparatus.

BACKGROUND ART

Human and animal embryos are presently cultured in controlled atmosphere incubators, with the aid of suitable growth-enhancing nutrients. The typical culturing cycle is three days, followed by implantation into the female reproductive system. Currently, there are several accepted methods which are practiced in the embryo culturing field. One of the generally accepted methods involves the use of Petrie dishes as a culturing container, in which individual embryos are placed. This technique involves submerging the individual embryos in respective drops of a growth-enhancing nutrient. Thus, each of the embryos is submerged in its own drop of the growth-enchancing nutrient. The practice of embryo culturing involves visually recording the morphology of the embryos and attempting to determine the viability of each embryo based on its morphology, and the position of certain features of the embryos such as R's polar bodies and spindles. This occurs in the culturing containers, and involves periodic visual inspection; note taking; and visual evaluation of the development of the embryos.

When the embryos are inspected as the embryos develop during the culturing period, the technician must obtain visual conformation as to which of the embryos may be more viable than the others, and which of the embryos are more likely to survive and further develop after implantation. This inspection requires that the technician physically remove the embryos in their Petrie dishes from the incubator, and carry them to a bench top location to be viewed through a microscope, or the like optical instrument. Another factor in the visual assessment of the embryos is that some country's governing bodies mandate by law that the selection process of the embryos to be implanted, (sometimes only three or fewer embryos), be made on the day of retrieval from the incubator. This is based on the then-existing morphological and physical characteristics of the embryos. The selected embryos may be the only embryos that are incubated through the entire culturing period, and then implanted. Flawed embryos that are detected during the culturing period are discarded.

As noted above, the embryos must be removed from the incubator environment and examined on a bench top by a microscope or other optical means. Subjecting the embryos to such relatively frequent handling is undesirable, but necessary in the culturing process as presently performed. Likewise, exposing the embryos to the ambient lab environment by removing the embryos from the specialized incubator environment is undesirable, but necessary in the culturing process as presently performed.

It would be desirable to provide an embryo or other specimen-culturing incubator assembly and process which allows the embryos or other specimens to be evaluated during the culturing period by a technician without having to remove the embryos or other specimens from the incubator during the culturing period.

DISCLOSURE OF THE INVENTION

This invention relates to an apparatus and method for culturing embryos, cells or other tissue specimens in a specimen growth-promoting environment. More specifically, this invention relates to an apparatus and method which allows monitoring of the condition of the specimens being cultured during the culturing period in situ without having to remove the specimens from the culturing environment. The culturing environment is preferably an incubator which has a controlled internal atmosphere and temperature. In one embodiment of the invention, the incubator is provided with one or more shelves on which the embryos being grown are situated. The incubator shelves are provided with receptor wells which are provided with visual embryo-imaging devices such as CCD's, or the like. The CCD's are operably connected to a computer, and/or to a visual monitor, which are used to record and/or display images of the embryos in embryo containers, which could be specially configured Petrie dishes, which images are periodically captured by the CCD's during the culturing period.

In certain cases, the receptor wells may also be provided with audio monitors which can sense and record sounds emanating from the specimens in the Petrie dishes. The technician who is monitoring the condition of the various embryos in the incubator can thus obtain visual and audio information from the culturing sites without having to remove the embryos from the incubator. A visual and audio histogram of the development of the embryos is thus provided for assessing the viability of each of the embryos for implantation.

In the case of embryo culturing, the embryos are placed in receptacles, such as Petrie dishes, which are placed in the growth-monitoring sites on the shelves in the incubator. The Petrie dishes can contain one, or more than one, embryo. The embryos in the Petrie dishes are immersed in a growth-promoting liquid which is formulated to provide an optimum opportunity for the embryos to develop to their fullest potential during the culturing period, which, as noted above, is typically about three days.

The apparatus and method of this invention thus provide for controlled monitoring of the viability of embryos, or other tissue specimens, being cultured in an incubator, without the need to periodically remove the specimens from the incubator.

The following is a listing of several desirable objects of this invention.

It is an object of this invention to provide a method and apparatus which is able to continuously observe the growth and morphology of embryos through the employment of audio and video transmitting and recording equipment connected to the inside a culturing incubator without removing the embryos from the incubator.

It is an another object of this invention to enable the study of embryos or other specimens while greatly minimizing movement of the specimens from the incubator thereby reducing the likelihood of an accident resulting from handling, and reducing the possibility of contamination from sources outside the incubator.

It is another object of this invention to provide visual and audio recording equipment in internal parts of the incubator for studying and evaluation of the specimens being cultured.

It is another object of this invention to provide internal power sources and probe attachments to the internal parts of the incubator to establish power and detection capabilities of the environment.

BRIEF DESCRIPTION OF THE DRAWINGS

These and other objects and advantages of the invention will become more readily apparent from the following detailed description of an embodiment of the invention, when taken in conjunction with the accompanying drawing in which.

DETAILED DESCRIPTION OF SPECIFIC EMBODIMENTS OF THE INVENTION

Figure 1:
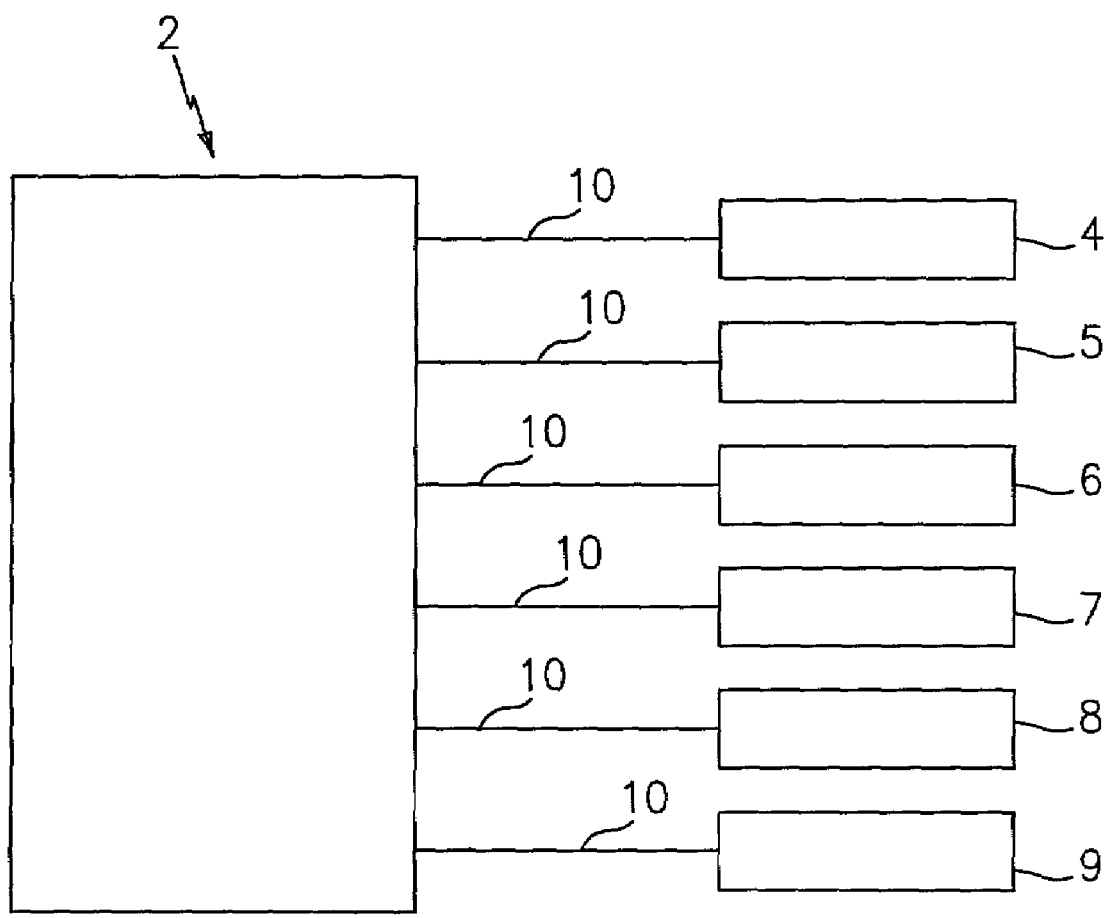
FIG. 1 is a schematic view of a tissue or embryo culturing system which is formed in accordance with this invention.

Referring now to the drawings, FIG. 1 is a schematic view of an incubation system which employs the concepts of this invention. The system includes an incubator 2 and a plurality of adjunct devices 4–9 which are electrically connected to the incubator 2 via lines 10. The adjunct devices 4–9 can include: a system processor controller; a video monitor; an audio monitor and recorder; incubator temperature and humidity controls and monitors; a signal digitizer; a telephone line for transmitting digitized signals to remote locations and/or for receiving incubator control instructions from remote locations; and other desired support equipment. The processor controller controls operation of the system, and establishes: the environmental conditions inside of the incubator 2; the timing of the imaging of specimens in the incubator 2; the capturing of the specimen images; and other system parameters.

Figure 2:
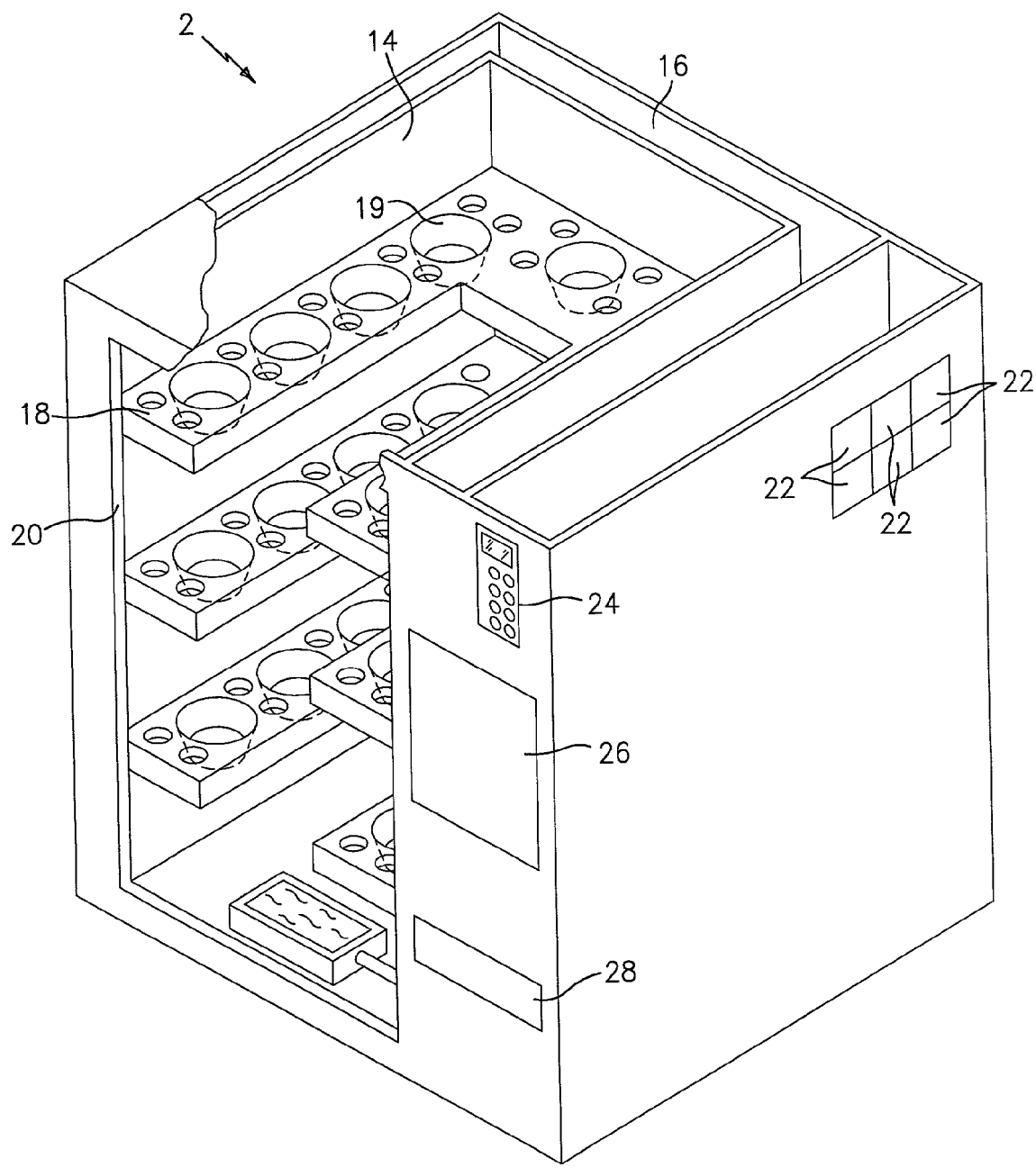
FIG. 2 is a fragmented schematic perspective view of an embryo-cufturing incubator, which is formed in accordance with this invention.

FIG. 2 is a schematic fragmented perspective view of the embryo culturing incubator assembly 2 which is formed in accordance with this invention. The incubator assembly 2 includes an inner compartment 14, which is inside of an outer jacket 16. The inner compartment 14 has a plurality of shelves 18 disposed therein, which shelves 18 include embryo-culturing wells 19 that, in turn, contain the embryo culturing dishes or cups (not shown). The incubator 2 includes an opening 20 through which its contents can be accessed. A plurality of adjunct device ports 22 are disposed on an outer wall of the incubator assembly 2 and are wired to the various active components inside of the incubator 2. A control panel 24 is mounted on the front wall of the incubator 2 and is operable to select the various operating parameters that will be put into effect by the processor controller. A readout panel 26 is also mounted on a front wall of the incubator 2. The readout panel confirms the selected operating parameters which are put in place at any particular time. A VHS tape or CD ROM port 28 is also included in the front wall of the incubator 2 for use in recording images of the specimens which are captured during the culturing period.

Figure 3:
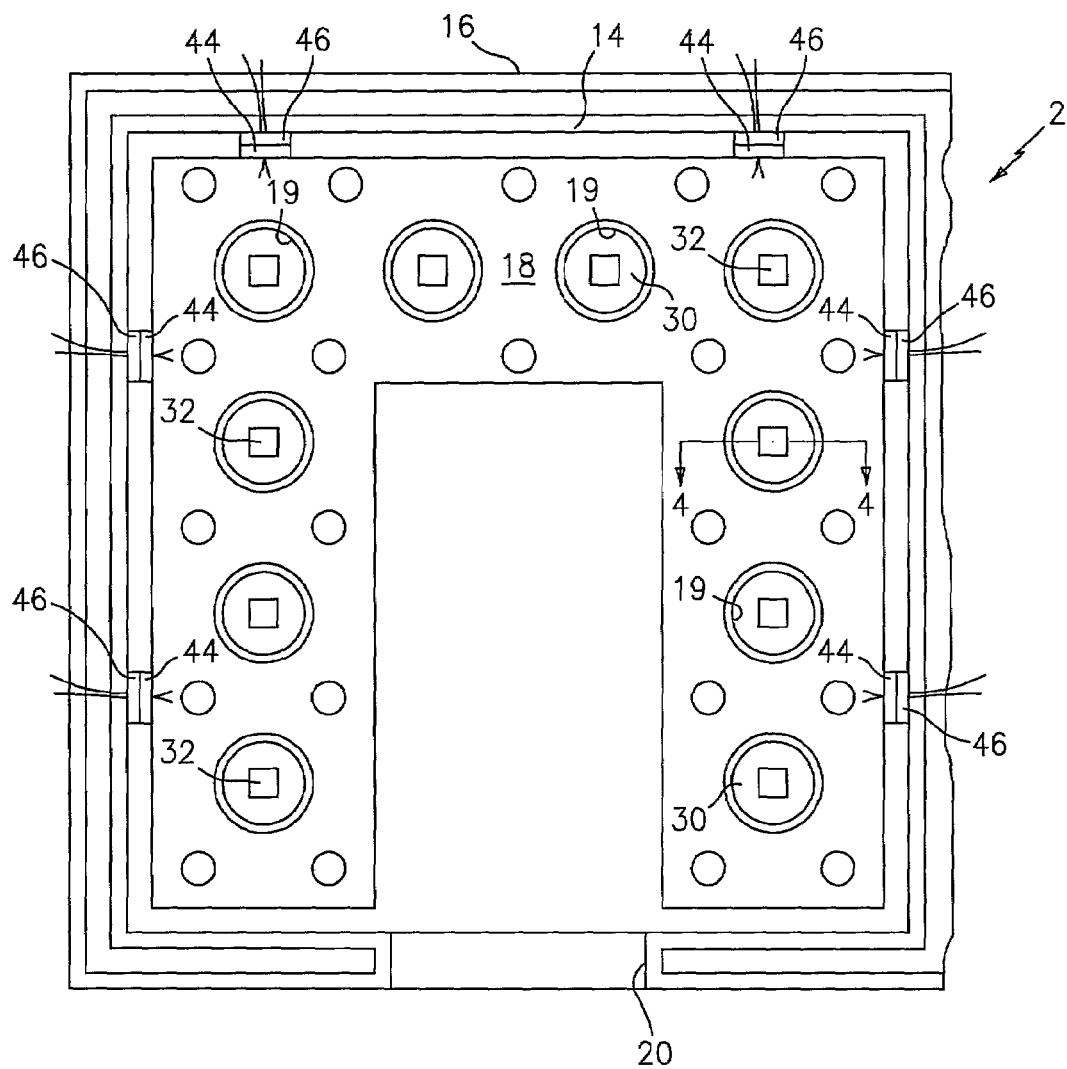
FIG. 3 is a plan view of a shelf assembly for an embryo-cufturing incubator, which shelf assembly is formed in accordance with this invention.
Figure 4:
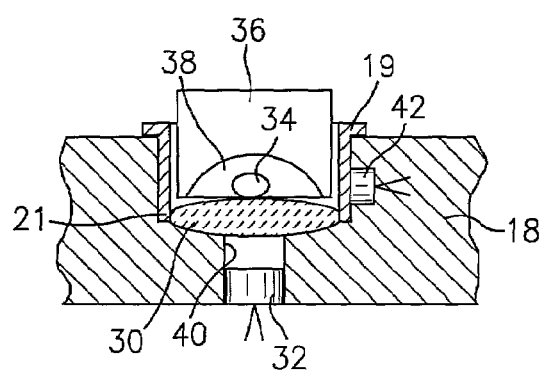
FIG. 4 is a sectional view of one of the wells in an incubator shelf assembly taken along line 4—4 of FIG. 2.

Referring now to FIGS. 3 and 4, the wells 19 include optical or digital lenses 30 which are preferably located at the bottom of each well 19. It will be noted that the wells 19 are preferably separate elements which are inserted into openings 21 in the shelves 18. The wells 19 will be formed from a transparent material such as tempered glass and the shelves 18 could be formed from stainless steel. Alternatively, the wells 19 could be integral with the shelves 18 if the shelves 18 are formed from the same transparent material as the wells 19. In the embodiment shown in FIGS. 3 and 4, each of the wells 19 will have a specimen image-capturing device 32, such as a CCD, mounted on the shelves 18 below the lenses 30.

Figure 5:
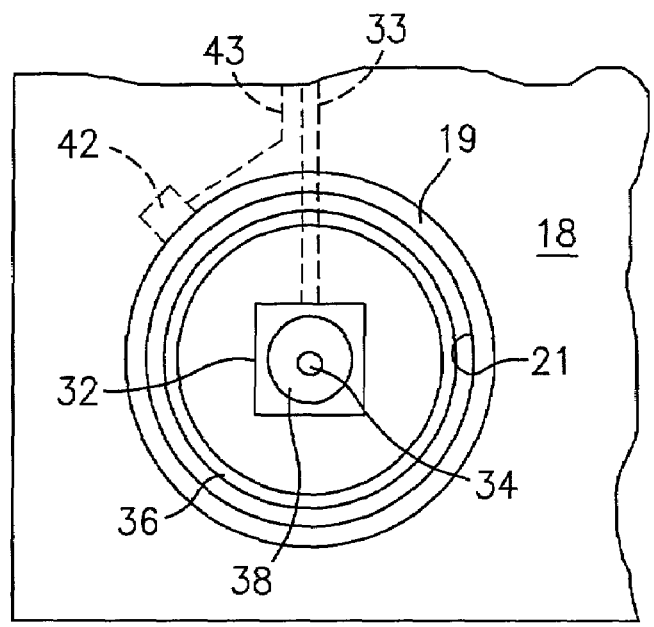
FIG. 5 is an enlarged fragmented plan view of one of the wells of the shelf assembly.

In the embodiment shown in FIGS. 3 and 4, the devices 32 are fixedly aligned with the lenses 21. The devices 32 are able to image the specimens 34 which are being cultured in the dishes 36 that are situated in the wells 19 through openings 40 in the shelves 18. Each of the specimens 34 will be immersed in a drop of culturing fluid 38 which promotes growth and development of each of the specimens 34. The shelf openings 21 may also be provided with audio monitors 42 which are able to monitor and transmit noises emanating from the dishes 36. The monitors 32 and 42 are electrically connected to the control and monitoring components of the system via the shelves 18 and the ports 22 in the following manner. The inner edges of the shelves 18 include electrical connectors 44 which are electrically connected to the well monitors or sensors 32 and 42. Mating electrical connectors 46 are provided on the inner wall 14 if the incubator 2. The connectors 46 are electrically connected to the adjunct ports 22 which are shown in FIG. 1. FIG. 5 shows the relative positions of the imaging device 32, the audio device 42, the specimen holder 36, the specimen 34, the culturing fluid 38, all relative to the well 19. The electrical connectors 33 and 43 for the imaging device 32 and the audio monitor 42, respectively, are also shown. The electrical connectors 33 and 43 are preferably disposed on the undersurface of each shelf 18 and lead to the connectors 44.

Figure 6:
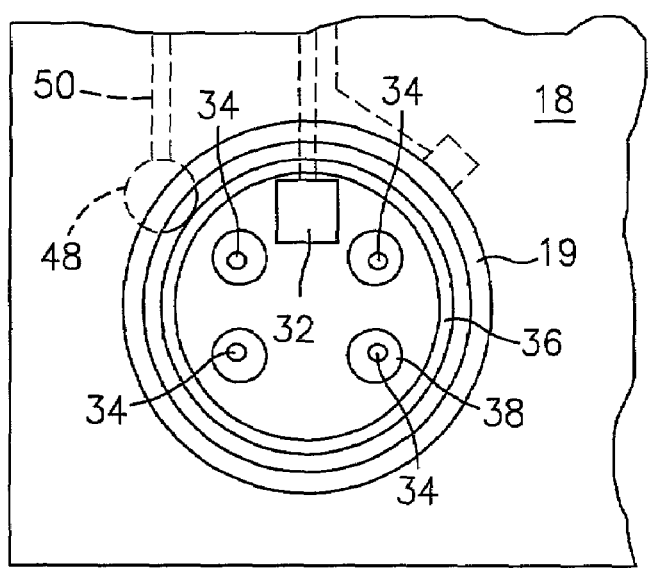
FIG. 6 is an enlarged fragmented plan view of a well in the shelf unit, which well is rotatable so as to facilitate selectively indexing of plural specimens in a container placed in the well, and align the specimens with an imaging device associated with the well.

FIG. 6 shows an alternate embodiment of the system, wherein the specimen containers 36 each contain a plurality of the specimens 34. The specimens 34 can be immersed in separate culturing fluid drops 38, or may all be immersed in a single culturing fluid drop 38. The specimens 34 can also be rendered immobile in the container 36 by use of the specimen corral structure described in co-pending U.S. patent application Ser. No. 09/590,389, filed Jun. 9, 2000. The wells 19 in the embodiment shown in FIG. 6 are rotatable in the shelves 18 so that the individual specimens 34 in the container 36 can be selectively indexed into alignment with the imaging device 32. Thus, the specimens 34 can be selectively periodically imaged by the system during the culturing period. Rotation of the wells 19 is accomplished by means of a selectively actuatable electric servo motor which drives a drive wheel 44. Electrical connectors 50 serve to provide power to the servo motors. The servo motors and the drive wheels 48 are mounted inside of the shelves 18 in frictional contact with the wells 19.

It will be readily appreciated that the system of this invention will allow individual biological specimens, such as embryos, tissue, cells, or the like, to be cultured in an incubator, and individual specimen development and viability parameters can be visually and audiologically monitored and recorded during the culturing procedure without the need to remove the specimens from the incubator environment. The invention allows the technician to identify the most robust specimens during the incubation period and to provide a visual histogram of each of the most robust specimens prior to removal from the incubator for in vivo implantation or further use.

Since many changes and variations of the disclosed embodiments of the invention may be made without departing from the inventive concept, it is not intended to limit the invention except as required by the appended claims.

What is claimed is:

1. An embryo specimen-culturing incubator assembly comprising:
    a) an embryo growth-supporting incubator, said incubator having a controlled internal atmosphere and having at least one specimen-supporting shelf containing a plurality of cup-shaped wells, said wells including transparent bottom walls;
    b) a plurality of optically transparent Petrie dish embryo specimen containers positioned in said incubator wells supported by said bottom walls of said wells, said containers containing at least one embryo culturing fluid drop; and
    c) embryo specimen growth-monitoring equipment associated with said incubator to visually monitor individual embryo specimen development in said container(s) through said bottom walls of said well(s) during an embryo specimen growth cycle, whereby individual embryo specimen development can be visually ascertained externally of the incubator without the need to remove the specimen container(s) from said incubator during said growth cycle, said growth-monitoring equipment including internal signal-producing optical imaging devices adjacent to said bottom walls of said well(s) in said incubator, and at least one external image signal-processing device outside of said incubator, which image signal-processing device converts signals from said imaging devices to visual images.

2. The assembly of claim 1 wherein said bottom walls of said wells include a lens for optically magnifying the embryo specimens in the specimen containers.

3. The assembly of claim 1 wherein said growth-monitoring equipment includes an internal audio signal-producing device adjacent to said container(s) in said incubator, and at least one external audio signal-processing device outside of said incubator, which audio signal-processing device is operable to record sounds emanating from specimens disposed in said specimen container(s).

4. The assembly of claim 1 wherein said containers are rotatable in said wells and further including one or more driver(s) for selectively rotating said containers and said wells so as to selectively align embryo specimens in said containers with said optical imaging device.

5. The assembly of claim 4 wherein there is a single optical imaging device adjacent to each of said container(s), said container(s) being sized to contain a plurality of embryo specimens, and said optical imaging device(s) being radially offset from an axis of said container(s), and wherein said driver(s) are operable to selectively and periodically align individual embryo specimens disposed in said container(s) with said optical imaging device(s) during said growth cycle.

6. The assembly of claim 1 wherein said optical imaging device(s) is (are) (a) CCD camera(s).

7. The assembly of claim 1 further comprising incubator temperature and humidity controls and monitors.

8. The assembly of claim 1 further comprising a system processor controller, a signal digitizer and a telephone line for transmitting digitized signals to remote locations and/or for receiving incubator control instructions from remote locations.

* * * * *